United States Patent
Munoz et al.

(10) Patent No.: US 10,751,003 B2
(45) Date of Patent: Aug. 25, 2020

(54) REDUCING MOTION-RELATED ARTIFACTS IN OPTICAL MEASUREMENTS FOR VITAL SIGNS MONITORING

(71) Applicant: Analog Devices Global Unlimited Company, Hamilton (BM)

(72) Inventors: Roberto Munoz, Alboraya (ES); Guillermo Serrano Leon, Jabaga (ES); Carlos Millan Navarro, La Vall d'Uixó (ES)

(73) Assignee: ANALOG DEVICES GLOBAL UNLIMITED COMPANY, Hamilton (BM)

(*) Notice: Subject to any disclaimer, the term of this patent is extended or adjusted under 35 U.S.C. 154(b) by 43 days.

(21) Appl. No.: 16/033,310

(22) Filed: Jul. 12, 2018

(65) Prior Publication Data
US 2020/0015753 A1    Jan. 16, 2020

(51) Int. Cl.
*A61B 5/02* (2006.01)
*A61B 5/00* (2006.01)
(Continued)

(52) U.S. Cl.
CPC ............ *A61B 5/725* (2013.01); *A61B 5/0059* (2013.01); *A61B 5/02416* (2013.01);
(Continued)

(58) Field of Classification Search
CPC . A61B 5/725; A61B 5/02416; A61B 5/02438; A61B 5/0531; A61B 5/0059; A61B 5/7203
See application file for complete search history.

(56) References Cited

U.S. PATENT DOCUMENTS

| 6,912,414 B2 | 6/2005 | Tong |
| 8,515,532 B2 | 8/2013 | Yin et al. |

(Continued)

FOREIGN PATENT DOCUMENTS

| WO | 2010023615 | 3/2010 |
| WO | 2017019184 | 2/2017 |

OTHER PUBLICATIONS

*Electrical (ECG) vs. Optical-Based (PPG) Biosensors in Wearable Devices*, NeuroSky®, 2015, www.neurosky.com, 3 pages.
(Continued)

*Primary Examiner* — Amanda K Hulbert
*Assistant Examiner* — Natasha Patel
(74) *Attorney, Agent, or Firm* — Patent Capital Group (57) ABSTRACT

Vital sign monitors are plagued by noisy photoplethysmography (PPG) data, making it difficult for the monitors to output consistently accurate readings. Noise in PPG signals is often caused by motion. The present disclosure provides improved techniques for reducing motion-related artifacts in optical/PPG measurements for vital signs monitoring. In general, techniques described herein are based on using measurements of reference sensors that include sensors other than optical sensors used for the optical measurements, e.g., biopotential sensors, bioimpedance sensors, and/or capacitive sensors. In particular, techniques described herein aim to filter PPG signals using substantially only the noise components of signals generated by reference sensors, by attenuating or altogether eliminating components of the signals generated by reference sensors which are indicative of the parameter the reference sensors are designed to measure. Implementing the techniques described herein may lead to more accurate vital sign evaluation using optical/PPG measurements.

23 Claims, 3 Drawing Sheets

(51) Int. Cl.
*A61B 5/024* (2006.01)
*A61B 5/053* (2006.01)

(52) U.S. Cl.
CPC ........ *A61B 5/02438* (2013.01); *A61B 5/0531* (2013.01); *A61B 5/7203* (2013.01)

(56) References Cited

U.S. PATENT DOCUMENTS

| | | |
|---|---|---|
| 9,326,733 B2 | 5/2016 | Kim et al. |
| 9,901,306 B2 | 2/2018 | Adams et al. |
| 9,943,266 B2 | 4/2018 | Adams et al. |
| 2007/0276270 A1* | 11/2007 | Tran ............... A61B 5/0476 600/508 |
| 2009/0227965 A1 | 9/2009 | Wijesiriwardana |
| 2011/0230745 A1 | 9/2011 | Chandrasekaran et al. |
| 2013/0310669 A1* | 11/2013 | Nitzan ............ G01N 21/3151 600/339 |
| 2013/0338724 A1* | 12/2013 | Joo ................. A61N 1/3987 607/3 |
| 2015/0216481 A1 | 8/2015 | Kim et al. |
| 2015/0282768 A1* | 10/2015 | Luna ............... A61B 5/721 600/301 |
| 2016/0029968 A1 | 2/2016 | Lerner et al. |
| 2016/0317097 A1* | 11/2016 | Adams ............. A61B 5/721 |
| 2017/0105682 A1 | 4/2017 | MacDonald |

OTHER PUBLICATIONS

Alper Comert et al., Investigating the possibleeffect of electrode support structure on motion artifact in wearable bioelectric signal monitoring, BioMed Eng Online (2015), 18 pages.

* cited by examiner

REDUCING MOTION-RELATED ARTIFACTS IN OPTICAL MEASUREMENTS FOR VITAL SIGNS MONITORING

TECHNICAL FIELD OF THE DISCLOSURE

The present disclosure relates to devices and methods for evaluating vital signs of living beings using optical measurements.

BACKGROUND

Modern electronics are ubiquitous in healthcare. For example, monitoring devices often include electronic components and algorithms to sense, measure, and monitor living beings. Monitoring equipment can measure vital signs such as heart rate, oxygen level in the blood, respiration rate, and so on. Not only are vital signs monitoring devices used in the clinical setting, but such devices are also used often in sports equipment and consumer electronics.

One important measurement performed by many of the monitoring equipment is heart rate, typically measured in beats per minute (BPM). Athletes use heart rate monitors to get immediate feedback on a workout, while health care professionals use heart rate monitors to monitor the health of a patient. Many solutions for measuring heart rate are available on the market today. For instance, electronic heart rate monitors can be found in the form of chest straps and watches. One technique often employed in wearable heart rate monitors is an optical measurement technique known as photoplethysmography (PPG).

In a PPG-based heart rate monitor, a signal indicative of a heart rate of a living being (said signal referred to in the following as a "PPG signal" or as a "heartbeat signal") is obtained by illuminating the skin (using a light source) of a living being, and measuring changes in light absorption (using an optical sensor). The principle of operation of PPG-based heart rate monitors are based on recognition that a heart rate can be measured passively or indirectly based on changes in light absorption in the skin of a living being as blood is pushed through the arteries. Changes in blood volume as blood is pumped through the arteries results in a variation in the amount of received light, which is translated into electrical pulses by an optical sensor. The pulses in the PPG signal can then be used in extracting a heart rate of the living being. Application of PPG measurements is not limited to measuring heart rate. In fact, PPG may be used to evaluate various other vital signs of living beings, such as blood pressure or perfusion.

Unfortunately, PPG-based electronic monitors are often not very accurate, largely due to a high amount of noise present in the signals provided by the sensors of these monitors. Noise is often caused by motion of a living being during the measurements and/or by movement of a measuring device with respect to the living being during the measurement. Such a noisy environment makes it difficult for the PPG-based monitors to output a consistently accurate vital sign reading and may lead to an irregular, inaccurate or even missing readout of the vital signs. One known technique for reducing motion-related artifacts (i.e., signal contributions due to motion of a living being) in PPG signals includes processing accelerometer readings that measure movement. Accelerometer measurements may help with filtering out some of the motion-related artifacts from PPG signals, but not always and not always to the desired degree. Therefore, improvements with respect to devices and methods for reducing motion-related artifacts from PPG signals used to determine various vital signs of living beings would be desirable.

BRIEF DESCRIPTION OF THE DRAWINGS

To provide a more complete understanding of the present disclosure and features and advantages thereof, reference is made to the following description, taken in conjunction with the accompanying figures, in which.

DESCRIPTION OF EXAMPLE EMBODIMENTS OF THE DISCLOSURE

Overview

The systems, methods and devices of this disclosure each have several innovative aspects, no single one of which is solely responsible for the all of the desirable attributes disclosed herein. Details of one or more implementations of the subject matter described in the present disclosure are set forth in the description below and the accompanying drawings.

As described above, vital sign monitors are plagued by noisy PPG data, which makes it difficult for the monitors to output consistently accurate readings. Noise is often caused by motion. Using known methods for processing accelerometer readings that measure movement to filter out some of this noise may help, but not always. Embodiments of the present disclosure provide improved techniques for reducing motion-related artifacts in optical/PPG measurements for vital signs monitoring. In general, techniques described herein are based on using measurements of sensors other than optical sensors used for the optical measurements. Such other sensors are referred to herein as "reference sensors" and may include one or more of, e.g., biopotential sensors, bioimpedance sensors, and capacitive sensors. In particular, techniques described herein aim to filter PPG signals using substantially only the noise components of signals generated by reference sensors, by attenuating or altogether eliminating components of the signals generated by reference sensors which are indicative of the parameter the reference sensors are designed to measure (e.g., if a reference sensor is a biopotential sensor, then the parameter the sensor is designed to measure is biopotential). Implementing any of the techniques described herein may lead to more accurate vital sign evaluation using optical/PPG measurements.

According to one aspect of the present disclosure, an apparatus for determining a vital sign, e.g., a heart rate, of a living being is disclosed. The apparatus may include a light source and an optical (light) sensor, configured to perform optical measurements on a portion of a tissue of a living being in order to evaluate the vital sign. Namely, the light source may be configured to generate light to illuminate a portion of a tissue of a living being, while the optical sensor may be configured to generate a first signal (e.g., a PPG signal), the first signal including a contribution (i.e., one or more signal components) referred to herein as a "tissue contribution," indicative of at least a portion of the light generated by the light source that has interacted with the tissue. Thus, the tissue contribution is indicative of at least a portion of the light generated by the light source that, e.g., penetrated into the tissue, possibly got diffused by the tissue or interacted with the tissue and blood therein in any other manner, and exited the tissue to be detected by the optical sensor. The "tissue contribution" may also be referred to as a heartbeat or blood flow contribution because it includes a contribution to the first signal that is due to the heartbeat activity of the living being and is, therefore, indicative of the heart rate of the living being. The apparatus may further include a reference sensor configured to generate a second signal, the second signal including a contribution referred to herein as a "reference contribution" and a contribution referred to herein as a "noise contribution". The reference sensor may e.g., be one or more of a biopotential sensor, a bioimpedance sensor, and a capacitive sensor. The reference contribution of the second signal refers to one or more signal components in the signal generated by the reference sensor that are indicative of the reference parameter that the sensor is intended to measure. For example, for a biopotential sensor, the reference contribution refers to one or more signal components indicative of the biopotential of the living being; for a bioimpedance sensor, the reference contribution refers to one or more signal components indicative of the bio-impedance of the living being, etc. On the other hand, the noise contribution of the second signal refers to one or more signal components in the signal generated by the reference sensor that is not directly indicative of the reference parameter that the sensor is intended to measure, but may be considered as noise. Such noise may, e.g., include typical noise generated by operation of various electronic components. Inventors of the present disclosure have further realized that such noise may also include information related to the movement of the living being and/or to the relative movement between the tissue of the living being that is being analyzed and the apparatus, i.e., motion-related noise. The apparatus may further include means for attenuating (e.g., reducing or eliminating) the reference contribution in the second signal to generate a filtered second signal (thus, the filtered second signal is the second signal in which the reference contribution is attenuated, leaving substantially only the noise contribution of the second signal in the filtered second signal) and means for subtracting the filtered second signal from the first signal to generate a filtered first signal. The apparatus may further include means for determining the vital sign, e.g., heart rate, based on the filtered first signal.

As used herein, a "signal generated by a sensor" includes not only signals as output by the sensor but also signals which have been processed in any manner after they have been generated by the sensor. Such processing may include, but is not limited to, analog-to-digital conversion, up- or down-sampling, certain filtering (e.g., to remove signal components which are known to be not needed for further processing), etc.

Other aspects of the present disclosure provide methods for operating such an apparatus and methods for determining a vital sign of a living being using an optical sensor and a reference sensor as described herein.

In the following, various embodiments of the present disclosure may be described with reference to a heart rate as an example of a vital sign, PPG as an example of an optical measurement, and a biopotential sensor as an example of a reference sensor. However, these descriptions are equally applicable to embodiments where optical measurements are optical measurements other than PPG, a vital sign is any physiological parameter of a living being that may be detectable using optical measurements as described herein, and a reference sensor is any other reference sensor other than that used for the optical measurements, all of which embodiments being within the scope of the present disclosure. For example, besides measuring/tracking a heart rate, embodiments of the present disclosure may be used to sense or measure other physiological parameters such as oxygen saturation (SpO2), blood pressure, respiratory rate, activity or movement, etc. Besides humans, the techniques described herein can be applied for evaluating/sensing other living beings such as animals.

As will be appreciated by one skilled in the art, aspects of the present disclosure, in particular aspects of reducing motion-related artifacts in optical measurements using reference sensor measurements as described herein, may be embodied in various manners—e.g., as a method, a system, a computer program product, or a computer readable storage medium. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by one or more hardware processing units, e.g., one or more microprocessors, of one or more computers. In various embodiments, different steps and portions of the steps of each of the methods described herein may be performed by different processing units. Furthermore, aspects of the present disclosure may take the form of a computer program product embodied in one or more computer readable medium(s), preferably non-transitory, having computer readable program code embodied, e.g., stored, thereon. In various embodiments, such a computer program may, for example, be downloaded (updated) to the existing devices and systems (e.g., to the existing vital sign monitoring apparatuses and/or their controllers, etc.) or be stored upon manufacturing of these devices and systems.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). The term "between," when used with reference to measurement ranges, is inclusive of the ends of the measurement ranges. The terms "substantially," "close," "approximately," "near," and "about," generally refer to being within +/−20% of a target value. Unless otherwise specified, the use of the ordinal adjectives "first," "second," and "third," etc., to describe a common object, merely indicate that different instances of like objects are being referred to, and are not intended to imply that the objects so described must be in a given sequence, either temporally, spatially, in ranking or in any other manner, The following detailed description presents various descriptions of specific certain embodiments. However, the innovations described herein can be embodied in a multitude of different ways, for example, as defined and covered by the claims or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

Other features and advantages of the disclosure will be apparent from the following description and the claims.

Understanding Issues of Vital Sign Monitors with Noisy Environment

For purposes of illustrating techniques for reducing motion-related artifacts in optical measurements using reference sensor measurements, as described herein, it is important to understand phenomena that may come into play when PPG is used to measure vital signs, such as a heart rate. The following foundational information may be viewed as a basis from which embodiments of the present disclosure may be properly explained. Such information is offered for purposes of explanation only and, accordingly, should not be construed in any way to limit the broad scope of the present disclosure and its potential applications.

Vital sign monitoring apparatuses, e.g., heart rate monitors, are often in direct contact with the skin/tissue of a living being. The monitors passively measure or track (i.e., measure continuously or repeatedly) heart rate by sensing one or more aspects of the tissue adjacent to the heart rate monitor. Due to the passive nature of such measurements, the optical sensor data can be affected by many sources of noise which can severely affect the ability of the heart rate monitor to determine an accurate heartbeat. These sources of noise can include external interference to the optical sensor, internal noise of the optical sensor and/or other electronic components within the heart rate monitor, motion causing disruptions in the optical sensor's capability in measuring the desired vital signs. Furthermore, heart rate monitors implementing optical sensors are affected by variability in the skin of different living beings and the variability of the skin and environment during the use of the heart rate monitor. All these different sources and issues have adverse impact on the heart rate monitor's ability to extract an accurate heart rate from optical measurements.

Figures 1, 2, 3:
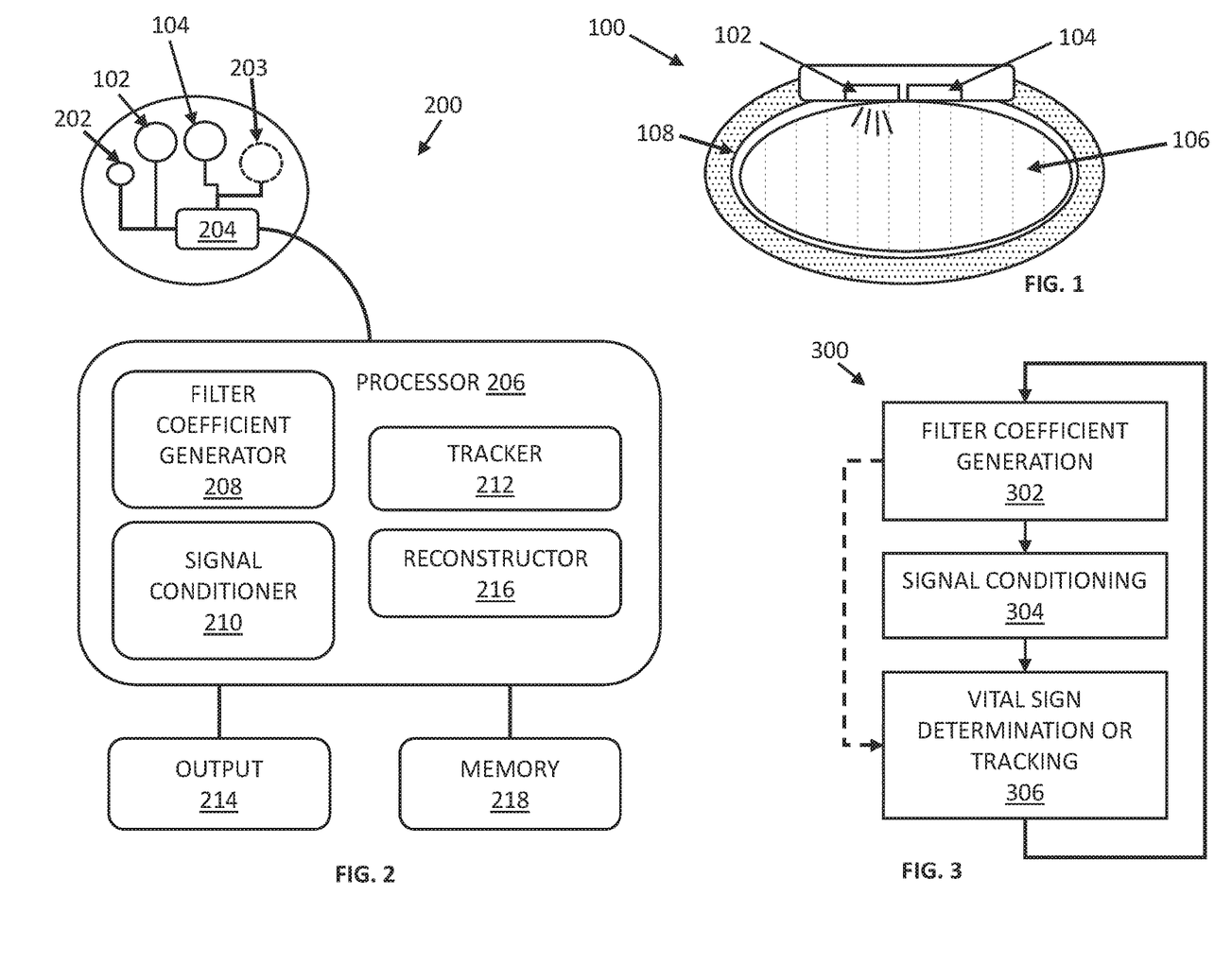
FIG. 1 shows an illustrative vital sign monitoring apparatus and a portion of a living being adjacent to the vital sign monitoring apparatus, according to some embodiments of the disclosure.
FIG. 2 illustrate a system view of a vital sign monitoring apparatus, according to some embodiments of the disclosure.
FIG. 3 illustrates an example flow diagram of a method for measuring vital signs based on input signals provided by one or more sensors of a vital sign monitoring apparatus, according to some embodiments of the disclosure.

FIG. 1 shows an illustrative heart rate monitoring apparatus 100 (or, in general, a vital sign monitoring apparatus or a monitor) and a portion of a living being adjacent to the heart rate monitor, according to some embodiments of the disclosure. In particular, FIG. 1 shows a cross section to illustrate the monitoring apparatus's spatial relationship with the portion of the living being. In this example monitoring setup, a PPG method is used, where the heart rate (or, in general, any suitable vital sign) is measured passively or indirectly based on changes in light absorption in the skin/tissue as blood is pushed through the arteries. Changes in blood volume as blood is pumped through the arteries results in a variation in the amount of light detected by an optical sensor of the monitor, which results in electrical pulses generated by the optical sensor. The pulses in the signal generated by the optical sensor of such a monitor can then be used in extracting a heart rate or other vital signs.

Monitoring apparatuses for evaluating vital signs based on optical measurements described herein are not limited to the particular example shown in FIG. 1. Although the disclosure does not describe other types of vital sign monitors in detail, one skilled in the art would appreciate that the challenges of noisy optical measurements affected by motion are also applicable in other types of vital sign monitors implementing optical measurements or other types of devices providing heart rate monitoring functions, or even devices utilizing other types of sensing mechanism. Furthermore, the continued process of measuring, following, extracting, determining, or sensing the heart rate (or some other vital sign) over time is referred to as "tracking" a vital sign, which is also within the context of the present disclosure.

Specifically, FIG. 1 illustrates an example heart rate monitoring apparatus 100 having a light source 102 and an optical sensor 104. The light source can emit light within a range of wavelengths suitable for the application. In some embodiments, the light source 102 and the optical sensor 104 can be provided separately. In some embodiments, the light source 102 can be biased to function as the optical sensor 104. For instance, a red light-emitting diode (LED) can be used as a red light source and a red optical detector. In some embodiments, both the light source 102 and the optical sensor 104 can be provided nearby each other in a housing or member of the heart rate monitoring apparatus 100 or in any suitable configuration where the optical sensor 104 can detect light generated by the light source 102 after said light has interacted with the part 106 of the living being. Various parts of the living being can be used as the part 106, e.g., a finger, an arm, a forehead, an ear, chest, a leg, a toe, etc., as long as changes in the volume of blood can be measured relatively easily. The part 106 can, in some cases, be internal to the body of the living being.

The light source 102 may be configured to shine a light onto a part 106 of a living being 106 and the optical sensor 104 can be configured to measure/detect light incident onto the optical sensor 104 and generate a signal, referred to herein as a "first signal" or a PPG signal, indicative of the detected light. The light detected by the optical sensor 104 can, and typically does, include various contributions. One contribution may be ambient light, i.e., light generated by sources other than the light source 102. Another contribution may be light that was generated by the light source 102 and was reflected by the part 106 to be incident on and detected by the optical sensor 104. Yet another contribution may be light that was generated by the light source 102 and interacted with the part 106 in a way other than simply being reflected from the part 106, e.g., light that penetrated into the tissue of the part 106, got diffused by the tissue, interacted with the tissue and blood therein, and exited the tissue to be detected by the optical sensor 104. It is typically the latter contribution to the light detected by the optical sensor 104, i.e., the light that was generated by the light source 102 and interacted with the part 106 in a way other than simply being reflected from the part 106, which is of the most interest for purposes of heart rate measurements. Different contributions to the light incident on and detected by the optical sensor 104 give rise to corresponding different contributions in the electrical signal generated by the optical sensor 104 as a result of sensing the incident light. Thus, the PPG signal generated by the optical sensor 104 may contain signal components (or contributions) caused by ambient light being incident onto the optical sensor 104, signal components caused by light that was generated by the light source 102 and was reflected by the part 106 before being incident onto the optical sensor 104, signal components caused by light that was generated by the light source 102 and interacted with the part 106 before being incident onto the optical sensor 104.

Generally speaking, if the heart rate monitoring apparatus 100 can be affixed to the part 106 of the living being securely and maintain relatively stable contact with the part 106 during use, the signal generated by the optical sensor 104 and provided as an input signal to a data processing stage would exhibit very little noise and the heart rate can be easily extracted. However, in many scenarios, the heart rate monitoring apparatus 100 is not securely affixed to the part 106 and/or the living being is moving, even with the use of part 108 involving a band, a strap, adhesive, or other suitable attachments, while, in other scenarios, having the apparatus 100 being securely adhered or attached to the part 106 is not desirable or comfortable for the living being. In these scenarios, the signal generated by the optical sensor 104 is usually affected by noise from ambient light, artifacts caused by motion of the heart rate monitoring apparatus, or by some other noise source. As a result, correctly detecting the heart rate in these non-ideal scenarios, i.e., in a noisy environment, can be challenging. Attempting to detect the heart rate based on a noisy signal generated by the optical sensor 104 can result in irregular or erroneous heart rate readings.

To address this issue, some heart rate monitoring apparatuses include a mechanism which discards certain portions of data generated by the optical sensor 104 if the data is deemed unusable for tracking the heart rate. The mechanism can include an accelerometer to measure the motion of the apparatus 100 to assess whether the signal generated by the optical sensor 104 is likely to be too degraded by motion artifacts to be relied upon for heart rate determination. In those cases, the accelerometer reading can cause the apparatus to discard data or freeze the heart rate readout when the accelerometer senses too much motion. However, this can be problematic for heart rate monitoring apparatuses which experiences a large amount of acceleration (e.g., in a sports setting), in which case the heart rate output may be either missing entirely or very inaccurate for a substantial amount of time during use. Some heart rate monitoring apparatuses include an accelerometer and then use accelerometer readings to filter the signal generated by the optical sensor 104 in an attempt to reduce motion-related artifacts in said signal. Such an approach may function reasonably well in some scenarios, but alternative and/or improved approaches for reducing motion-related artifacts in PPG signals would be desirable in more challenging scenarios where the accelerometer data may not provide sufficient help.

Reducing Motion-Related Artifacts in PPG Signals Using Reference Sensor Measurements The present disclosure describes an improved front end processing mechanism that may alleviate some of the issues with noisy PPG signals mentioned above. The improved mechanism is a filtering mechanism that allows for a more nuanced processing of the signal generated by the optical sensor 104 and can enable the signal to be conditioned in such a way as to allow determination of a heart rate, or other vital signs, even when the signal was acquired in a noisy setting. By improving on the filtering mechanism, the heart rate monitoring apparatus can achieve more robust performance in a noisy environment. An improved filtering mechanism can increase the amount of the usable data and thereby increase the accuracy and consistency of the heart rate output. Furthermore, the improved filtering mechanism can improve the accuracy of a tracking mechanism that may be implemented by the heart rate monitoring apparatus for tracking the heartbeat, by way of providing a better and more usable input signal.

The improved filtering mechanism described herein utilizes reference sensors, i.e., sensors other than the optical/PPG sensor 104 (e.g., biopotential sensors, bioimpedance sensors, or capacitive sensors), to filter the signal generated by the optical sensor 104 in an attempt to remove motion-related artifacts from such a signal. In particular, various embodiments of the present disclosure are based on recognition that at least some of the noise present in measurements of a reference sensor, e.g., noise present in biopotential measurements, may be related to the motion that affects the optical sensor 104 used to perform optical measurements based on which vital signs of a living being may be determined, e.g., related to the motion that affects PPG measurements. In fact, inventors of the present disclosure have found a strong correlation between motion-related artifacts in PPG signals from the optical sensor 104 and motion-related artifacts in reference sensor signals, e.g., in measurements performed by a biopotential sensor. Inventors of the present disclosure further discovered that performing measurements on a living being using a suitable reference sensor, e.g., a biopotential sensor, then filtering the reference sensor readings in an attempt to get rid of the signal contributions related to the actual parameter (e.g., biopotential) being measured, leaving substantially only the noise contributions in filtered reference sensor readings (i.e., signals), and using the filtered reference signal readings to filter PPG readings provides a substantial improvement in reducing motion-related artifacts in PPG readings compared to conventional techniques such as using accelerometer measurements.

The approach described herein may seem counterintuitive in that reference sensor measurements are obtained but then signal contributions related to the actual parameter being measured by a reference sensor are attempted to be minimized. Again, this is based on inventors' recognition that what it is relevant for extracting, isolating, or assessing the effect of the motion on a PPG signal is not really the biopotential, bioimpedance, or capacitance itself (i.e., not the actual parameter being measured by a reference sensor), but, rather, alterations that the motion of the one or more electrodes of a reference sensor produces in the measurements carried out by the reference sensor, which alterations are closely related to the motion of the PPG sensor. In other words, the biopotential, bioimpedance, or capacitance that is intended to be measured by a given reference sensor is not changing with motion, but the measured values of these parameters do change with motion, e.g., because there is a change in the contact resistance to the one or more electrodes of the reference sensor. The improved filtering mechanism described herein leverages an insight that, provided that a reference sensor is in relatively close proximity to a PPG sensor (e.g., the optical sensor 104) of the monitoring apparatus so that both the reference sensor and the PPG sensor experience the same motion, reference sensor measurements acquired substantially at the same time (or in a time-overlapping manner) as the measurements by the PPG sensor may be considered to accurately represent motion of the PPG sensor when the PPG signal was acquired. In turn, reference sensor measurements may be used in reducing the amount of noise in the PPG signal by reducing at least some of the motion-related artifacts in the PPG signal. In particular, applying an adaptive algorithm attempting to isolate noise contributions in the reference sensor readings allows creating a filter that may reduce or eliminate motion-related artifacts from the PPG signal acquired by an optical sensor. As a result, identification/tracking of the heartbeat signal from a noisy PPG signal, and determination of a heart rate or other vital signs from the PPG signal, may be improved. The following passages describe in further detail some embodiments of how the improved filtering mechanism can be implemented and realized.

Example Apparatus and Method for Reducing Motion-Related Artifacts in PPG Signals FIG. 2 illustrates a system view of a vital sign, e.g., heart rate, monitoring apparatus 200, according to some embodiments of the disclosure. The system provides an arrangement of parts for implementing or enabling a method for reducing motion-related artifacts in optical/PPG measurements using reference sensor measurements. Although not specifically shown in FIG. 2, the apparatus 200 of FIG. 2 may be used with a part 106 of a living being as described above for the apparatus 100. In the interests of brevity, those descriptions are not repeated here, but all of the descriptions provided for the apparatus 100 are applicable to the apparatus 200, unless specified otherwise.

Similar to FIG. 1, the apparatus 200 includes a light source 102, an optical sensor 104. The light source 102 can be an LED, or any suitable component for emitting light. The light emitted by the light source 102 for measuring heart rate (e.g., blood volume) or other appropriate vital signs can be of any suitable wavelength depending on the application. The light source 102 of the apparatus 200 can include a plurality of light sources emitting one or more ranges of wavelengths of light. The optical sensor 104 may be the same device as the light source 102 (e.g., by being biased differently to operate as a light sensor or a light emitter), or the optical sensor 104 may be provided near the light source 102 within a housing of the apparatus 200, to measure light near the optical sensor 104, e.g., to measure absorption of light emitted by the light source 102 in the tissue of a living being to implement PPG.

In addition, as shown in FIG. 2, the apparatus 200 includes a reference sensor 202 configured to perform measurements of other parameters on a portion of a tissue of the living being, e.g., on or near the part 106 of a living being. In some embodiments, the reference sensor 202 may be a biopotential sensor configured to measure biopotential on a portion of a tissue of a living being. In some embodiments, the reference sensor 202 may be a bioimpedance sensor configured to measure bioimpedance on a portion of a tissue of a living being. In some embodiments, the reference sensor 202 may be a capacitive sensor configured to measure capacitance between the sensor 202 and a portion of a tissue of a living being. In some embodiments, the reference sensor 202 may include one or more of any of such sensors. Furthermore, the apparatus 200 may, optionally, include other sensors 203 or other types of sensors, which can provide information to assist in filtering of the PPG signal and/or vital sign determination or tracking. For example, the sensor 203 may include an accelerometer to measure acceleration/motion of the overall apparatus 200.

A biopotential sensor may be any sensor configured to perform biopotential measurements, e.g., as used in modern medical procedures. This sensor measures electrical activity in the body, so depending on its location, gain, and bandwidth, it can be used to obtain electrocardiogram (ECG), electroencephalogram (EEG), electromyography (EMG), etc. ECG lead systems can be used to obtain biopotential signals containing information indicative of the electrical activity associated with the heart and circulatory system. For example, to obtain an ECG signal using a biopotential sensor, electrodes may be applied to the skin of a patient in various locations and coupled to an ECG monitor. A biopotential analog front end may include an instrumentation amplifier (i.e., a differential amplifier with the highest common mode rejection ratio), which may be capacitively coupled to the living being to block unwanted direct current (DC) potential signals.

A bioimpedance sensor may be any sensor configured to perform bioimpedance measurements, e.g., as used in modern medical procedures. Bioimpedance may be measured injecting a known current between two electrodes connected to the skin of a living being and measuring the voltage drop (between these two electrodes or two nearby electrodes) or by applying a known voltage drop and measuring current flow. This excitation and measurement may be executed with 2-wire and 4-wire techniques. Depending on the frequency of the current applied, the current may flow deeper inside the tissue. Bioimpedance may be used to estimate hydration level, stress, and/or dermatological conditions.

A capacitive sensor may be any sensor configured to perform capacitive measurements on a portion of a tissue of a living being by measuring the capacitance of a parasitic capacitor between a conductive plane located in the capacitive sensor (i.e. sensor electrode) and the internal ground plane of the sensor. The capacitance will change depending on the variation in the dielectric which is formed by the gap between these two planes, including the skin and tissue underneath. A capacitive sensor may be implemented in many ways, known in the art, all of which being within the scope of the present disclosure. In some embodiments, a capacitive sensor may be part of a relaxation oscillator and then frequency of the relaxation oscillator is indicative of capacitance. In other embodiments, capacitance can be derived based on applying a fixed-frequency AC-voltage to a capacitive driver of a capacitive sensor. In still other embodiments, capacitance can be derived based on measuring the time it takes to charge the capacitor to a certain threshold using a constant current source.

An integrated circuit can be provided to drive the light source 102 and provide an analog front end (AFE) 204 to receive signals provided by the optical sensor 104, the reference sensor 202, and other sensors 203. In some embodiments, the AFE 204 can convert (if desired) analog input signals (e.g., analog signals generated by the optical sensor 104, the reference sensor 202, and other sensors 203) to data samples of digital signals. The AFE 204 can be communicatively coupled with a processor 206 to provide the data samples, which the processor 206 would process to determine and/or track a vital sign of interest, e.g., the heart rate of the living being.

In various embodiments, the processor 206 can include several special application specific parts or modules, electronic circuits, and/or programmable logic gates specially arranged for processing the data samples of the input signals (i.e., data samples of a first signal generated by the optical sensor 104 and a second signal generated by the reference sensor 202), to determine one or more vital signs of interest. The processor 206 can be a digital signal processor provided with application-specific components to determine vital signs of interest, and/or the processor 206 can execute special instructions (e.g., stored on non-transitory computer readable-medium) for carrying out various embodiments of a method for determining vital signs of interest from PPG signals in combination with reference sensor measurements as described herein. FIG. 3 illustrates an example flow diagram of one such a method 300, e.g., implemented by the processor 206 shown in FIG. 2, for determining vital signs of interest, according to some embodiments of the disclosure. At a high level, the method 300 may include a filter generation stage 302, a signal conditioning stage 304 (dependent on the filter generation stage 302), and a stage 306 for determining and/or tracking a vital sign of interest (dependent on the filter generation stage 302 and/or the signal conditioning stage 304). In some embodiments, the method 300 can be performed iteratively (as indicated in FIG. 3 with an arrow from the stage 306 to the stage 302) to process other data samples in the stream of data samples generated by the optical sensor 104 and the reference sensor 202, or to adaptively improve filtering applied on the data samples, as described herein.

Referring to both FIG. 2 and FIG. 3, in some embodiments, the parts of processor 206 can include one or more of the following: a filter coefficient generator 208, a signal conditioner 210, a tracker 212, and a reconstructor 216, e.g., to implement the method shown in FIG. 3.

The filter coefficient generator 208 may be configured to implement functions related to the improved filtering mechanism (corresponding to filter generation stage 302 of the method 300 shown in FIG. 3) by using reference sensor measurements to filter the PPG signal generated by the optical sensor 104 before providing the data samples of the PPG signal to the tracker 212.

The signal conditioner 210 may be configured to implement functions related to processing data samples of the input signals based on the decision(s) in the filter coefficient generator 208 to prepare the data samples for further processing by the tracker 212 (corresponding to signal conditioning stage 304 of the method 300 shown in FIG. 3). For instance, the signal conditioner 210 can be configured to filter data samples of the input signals a certain way (or apply a filter on the data samples), apply a mask to the data samples, attenuate certain data samples, modify the values of certain data samples, and/or select certain data samples from a particular sensor for further processing. The signal conditioning process can depend on the output(s) of the filter coefficient generator 208. In particular, the signal conditioner 210 may use the filter coefficients generated by the filter coefficient generator 208 to filter data samples of the input signals.

The tracker 212 may be configured to implement functions related to determining, and, optionally, tracking the vital signs of interest, e.g., the heart rate of the living being, based on the output from the signal conditioner 210 (corresponding to vital sign determination and/or tracking stage 306 of the method 300 shown in FIG. 3). In some embodiments, the tracker 212 may be configured to continuously monitor the incoming data samples (e.g., either raw data provided to the processor 206 from the AFE 204 or directly from the optical sensor 104 and the reference sensor 202, or data as provided by the signal conditioner 210) and attempt to continuously determine the vital sign of interest from the sensor signals. In some embodiments, the output of the tracker 212 represents an estimate of the vital sign of interest, e.g., an estimate of a heart rate in BPM, and can be provided to a user via an output 214 (e.g., a speaker, a display, a haptic output device, etc.). In other embodiments, the output 214 may include a filtered version of the PPG signal, e.g., as provided at an output of the signal conditioner 210, or an output of the reconstructor 216.

The reconstructor 216 may be configured to implement functions related to (re)constructing or synthesizing a representation of the vital sign(s) of interest, e.g., a heartbeat. Based on the outputs of one or more of the filter coefficient generator 208, the signal conditioner 210, and the tracker 212, the reconstructor 216 can artificially generate a cleaner version of the PPG signal (i.e., a reconstructed PPG signal). The reconstructed signal can be useful in many applications. For instance, the reconstructed signal can be provided to the output 214 for display. The reconstructed signal can also be saved, e.g., in memory 218 of the apparatus 200, for later processing and/or viewing. Generally speaking, the reconstructed signal can be useful for users to visually and analytically assess the health of a living being with the irrelevant noise content removed. For instance, the reconstructed signal can assist healthcare professionals in assessing whether the living being has any underlying conditions relating to heart and arterial health.

The filter coefficient generator 208, the signal conditioner 210, the tracker 212, and the reconstructor 216 can include means for performing their corresponding functions. Data and/or instructions for performing the functions can be stored and maintained in memory 218 (which can be a non-transitory computer readable medium). In some embodiments, the filter coefficient generator 208 (corresponding to filter generation stage 302 of the method 300 shown in FIG. 3) can affect the processing performed in tracker 212 (corresponding to vital sign determination and tracking stage 306 of the method 300 shown in FIG. 3). This feature is denoted in FIG. 3 by the arrow having the dashed line. The apparatus 200 shown in FIG. 2 is merely an example of a vital sign monitoring apparatus that can implement various embodiments of the present disclosure, it is envisioned that other suitable arrangements can be provided to implement the improved method for reducing motion-related artifacts in noisy optical measurements using reference sensor measurements.

Filtering of PPG Signals Using Reference Sensor Measurements

A filter conditions an incoming signal and produces an output signal having certain selected or controlled characteristics. Coefficients of a filter determine its characteristics and output. Often, a specific output may be desired, but the coefficients of the filter cannot be determined at the onset. One example is an echo canceller where the desired output cancels the echo signal. In such a case, oftentimes the coefficients cannot be determined initially because they depend on changing transmission conditions. For such applications, one option may be to rely on adaptive filtering techniques.

An adaptive filter refers to a time-varying filter whose coefficients are adjusted in a way to optimize a cost function or to satisfy some predetermined optimization criterion. An adaptive filter may be considered to include two distinct parts: 1) a filter itself, where the structure of the filter is designed to perform a desired processing function, and 2) an adaptive algorithm configured to adjust the coefficients of the filter to improve its performance. The filter structure and the adaptive algorithm used in a particular adaptive filter depend on various design characteristics and acceptable trade-offs, such as e.g., a trade-off between accuracy and complexity of a filter.

Figure 4:
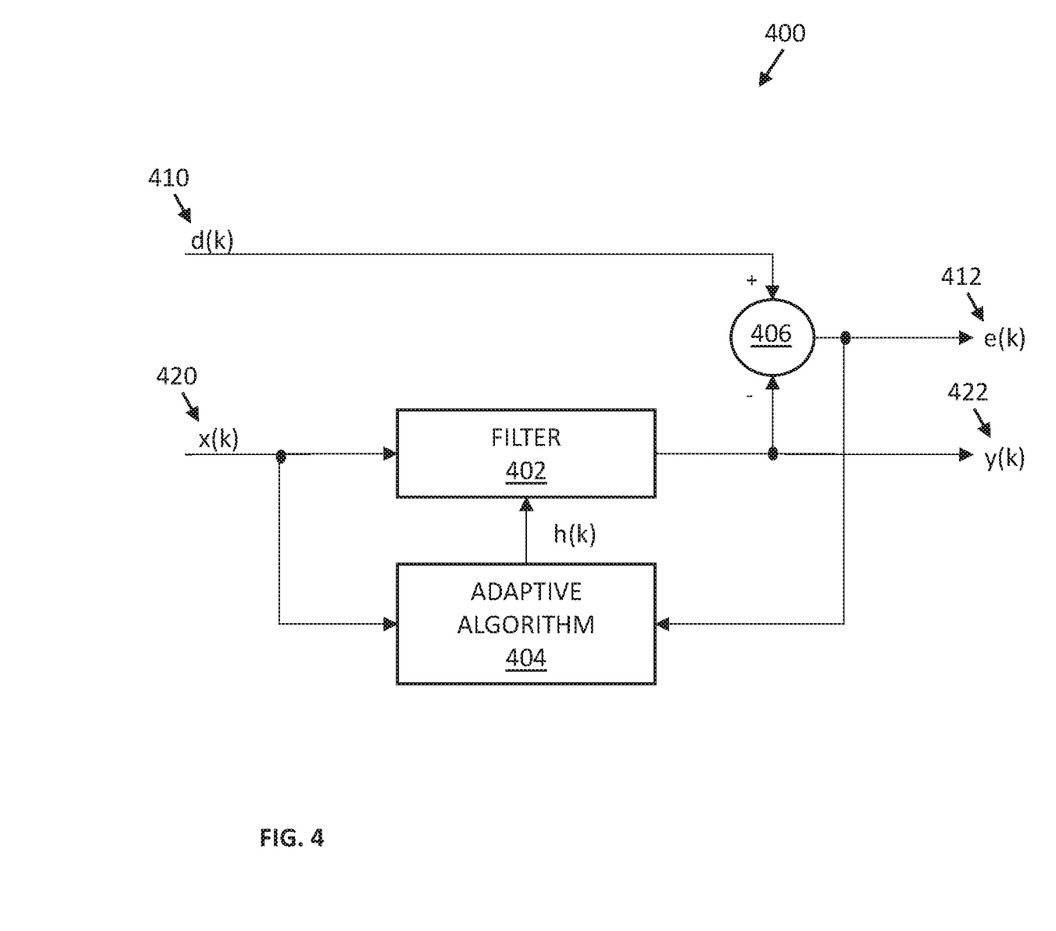
FIG. 4 illustrates a schematic diagram of an example of an adaptive filter arrangement that may be used for evaluating vital signs of a living being, according to some embodiments of the disclosure.

FIG. 4 illustrates a schematic diagram of an example of an adaptive filter arrangement 400 that may be used for evaluating vital signs of a living being, according to some embodiments of the disclosure. As shown in FIG. 4, the adaptive filter arrangement 400 may include a filter 402 and an adaptive algorithm 404. Two input signals may be provided to the adaptive filter arrangement 400. A first input signal, d(k), is a PPG signal 410 generated by the optical sensor 104 of the vital sign monitoring apparatus 200. A second input signal, x(k), is a reference sensor signal 420 generated by the reference sensor 202 of the vital sign monitoring apparatus 200. As defined before, a "signal generated by a sensor" may not necessarily be a raw signal as output from a sensor, but may be a pre-processed signal. The first and second such signals 410, 420 are shown in FIG. 4 to be as digital signals, e.g., as converted by the AFE 204 of the vital sign monitoring apparatus 200.

Each of the first and second signals 410, 420 include various contributions. In particular, the first signal 410 includes a tissue contribution indicative of at least a portion of the light generated by the light source 102 after said portion of light has interacted with a tissue of the part 106. This contribution is what allows determining a heart rate, or other vital signs, from the first signal 410. The first signal 410 also includes a noise contribution, due to various sources of noise as described above, including motion-related artifacts. This contribution is what impedes determination of the heart rate. Similarly, the second signal 420 includes a reference contribution indicative of the reference parameter that the reference sensor 202 is intended to measure, e.g., biopotential. The second signal 420 also includes a noise contribution, due to various sources of noise. Inventors of the present disclosure have identified a strong correlation between the noise contribution in the second signal 420 and the noise contribution in the first signal 410. Namely, inventors of the present disclosure realized that the noise contribution of the second signal 420 may be used to filter the first signal 410. To that end, the filter 402 may be configured to filter the second signal 420 in an attempt to reduce, e.g., completely eliminate or reduce as much as possible, the reference contribution in the second signal 420, generating a filtered second signal 422, y(k), that contains substantially only the noise contribution. The filtered second signal 422 may then be provided to a second filter 406, which may, e.g., be a subtractor, to filter the noise contribution out of the first signal 420, thus generating a filtered first signal 412, e(k), in which the noise contribution is attenuated.

In some embodiments, such filtering may be performed iteratively, in order to update filter coefficients used by the filter 402 in the face of changing environments and changing system requirements to more accurately perform the desired filtering of attenuating the reference contribution in the second signal 420. To that end, the filtered first signal 412 may be provided to the adaptive algorithm 404 which is configured to automatically adapt (i.e., self-optimize) to perform specific filtering and decision-making tasks according to suitably selected update equations that define the training rules, e.g., to minimize energy in the filtered first signal 412 and/or to minimize reference contribution in the filtered second signal 422.

In some embodiments, the second signal 420 may be applied to a shift register or other memory device implemented in the filter 402, and the filtered second signal 422 may include a weighted sum of current and past samples of the second signal 420. The adaptive algorithm 404 may adjust the weights (i.e., the coefficients) in the filter 402 to minimize the energy in the filtered first signal 412, e(k), which may be a difference between the first signal 410 and the filtered second signal 422, by providing an impulse response 408, h(k), of an adaptive filter to the filter 402.

In some embodiments, the filter 402 may be a finite impulse response (FIR) filter with M taps. In some embodiments, the adaptive algorithm 404 may be a least mean square (LMS) algorithm, a power-normalized LMS algorithm or any other variation of LMS algorithms. Although not specifically shown in FIG. 2, the vital sign monitoring apparatus 200 may include a power estimation element configured to estimate energy/power of the filtered first signal 412, which values are then provided to the adaptive algorithm 404.

In some embodiments, the adaptive filter arrangement 400 may include a sample delay, e.g., a single sample delay $Z^{-1}$, introduced before the filter 402, to ensure that the filter 402 only has access to past data samples of the second signal 420, where variable "Z" is used in this example to denote that "Z" may stand for a Z-transform which is similar to the Laplace transform for continuous-time circuits except that in this case it is optimized for discrete-time processing used whenever the data is in a sampled form. Thus, in general, $Z^{-m}$ represents an m-sample delay that may be provided before the filter 402. Variable m being equal to 1 indicates a single sample delay, but m could also be greater than one sample, which may be advantageous in some applications in view of the design trade-offs as known in the art.

For the example illustration of FIG. 4, the update equation for the kth FIR coefficient (denoted "c") at time n (i.e., for the nth data sample of the second signal input X) may be expressed as follows:

$$c(n+1)=c(n)+\text{alpha}*x(n)*\text{err}(n)/\text{power}(n),$$

where x(n) are the input values stored in the FIR shift register of the filter 402 at time n, c(n) are the coefficients of the FIR filter at time n, err(n) is the prediction error at time n (i.e., the filtered first signal 412?), alpha is a constant that controls the convergence rate, and power(n) is the average input signal power averaged over the length of the FIR filter. C(n) and x(n) are vectors, and err(n) and power(n) are scalars; alpha is a scalar constant.

Figure 5:
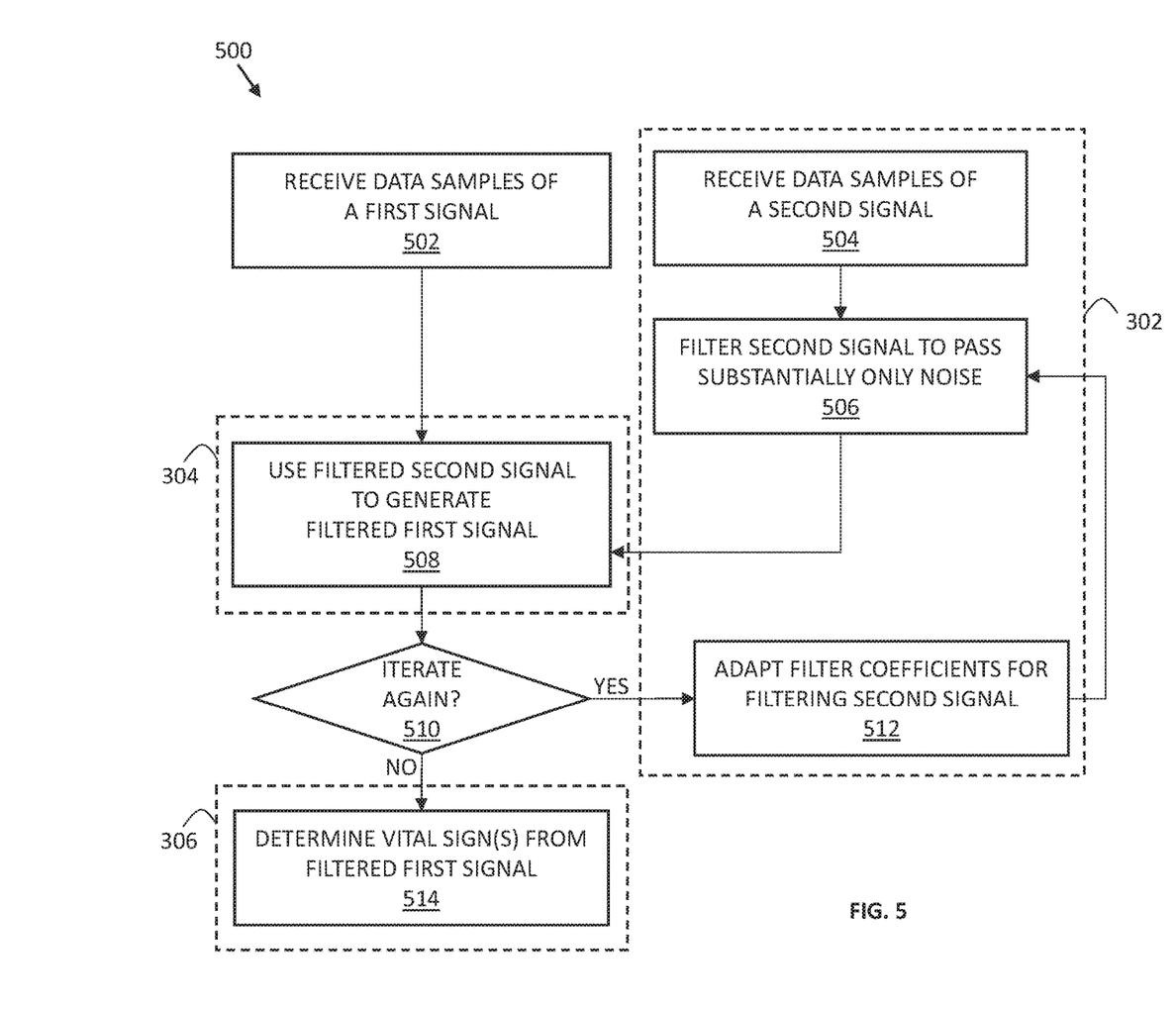
FIG. 5 illustrates an example flow diagram of a method for using reference sensor measurements for reducing motion-related artifacts in PPG signals, according to some embodiments of the disclosure.

FIG. 5 illustrates an example flow diagram of a more detailed method 500 for using reference sensor measurements for reducing motion-related artifacts in PPG signals, according to some embodiments of the disclosure. While the method 500 is described with reference to FIGS. 2 and 4, any system or apparatus configured to perform processes of the method 500, in any suitable order, is within the scope of the present disclosure.

As shown in FIG. 5, at a process 502, the method 500 includes a processor, e.g., the processor 206, receiving data samples of a first signal generated by an optical sensor. The first signal received at 502 can be the first signal 410 generated by the optical sensor 104, and in some cases, the first signal is processed by an analog front end, e.g., the AFE 204, to produce (digital) data samples of the first signal, before being received by the processor 206.

The method 500 also includes a process 504 which includes a processor, e.g., the processor 206, receiving data samples of a second signal generated by a reference sensor. The second signal received at 504 can be the second signal 420 generated by the reference sensor 202. Similar to the first signal, in some cases, the second signal is processed by an analog front end, e.g., the AFE 204, to produce (digital) data samples of the second signal, before being received by the processor 206. Preferably, the second signal received at 504 is acquired substantially at the same time as the first signal received at 502, and the two signals are processed synchronously, thus providing the closest overlap between the motion information from the noise contribution of the reference sensor and the motion-related artifacts in the first signal acquired by the optical sensor. The data samples of the second signal are received by the processor for adaptive filter operation.

Leveraging the insight that the noise contribution in the signal generated by a reference sensor taken substantially at the same time as the measurements by an optical PPG sensor may be considered to accurately represent motion of the optical sensor when the first signal was acquired, the processor 206 may enable filtering of the data samples of the second signal to pass substantially only the noise contribution and attenuate the reference contribution in the second signal, in a process 506 shown in FIG. 5. To that end, adaptive linear prediction may be used, where the filtered second signal generated in the process 506 is used to generate a filtered first signal at a process 508, e.g., by subtracting the filtered second signal 422 from the first signal 410, determining, at a process 510, whether another iteration is to be performed, and, in response to a positive determination at the process 510, adapting filter coefficients, at a process 512, for filtering the second signal, which adapted coefficients are then used in the next iteration of the process 506. Thus, a sequence of the processes 506, 508, 510, and 512 may be performed iteratively (i.e., multiple times) as long as the determination of the process 510 is positive.

In some embodiments, the number of iterations to be performed (and thus, the decision made in the process 510) may be a certain predefined, or dynamically defined number, e.g., defined by the processor 206 and/or stored in the memory 218. In other times, iterations are performed until a certain criteria is met, e.g., until the filtered first signal power is minimized to be within a certain range.

In still other embodiments, the process 510 is not included because adaptation process of adapting coefficients is performed on a per-sample manner and vital signs are attempted to be determined each time. For example, in such embodiments where the process 510 is not included in the method 500, from the process 508, the method 500 may proceed to the process 512 where filter coefficients are adapted for filtering the second signal the next time filtering takes place (e.g., for the next sample of the second signal), and the method 500 also proceeds to the process 514 where the latest version of the filtered first signal 412 is used by the processor 206 to determine one or more vital signs, in a process 514.

Whether the process 510 is included or not, a process 514 includes that the filtered first signal, e.g., the latest version of the filtered first signal 412, is used by the processor 206 to determine one or more vital signs.

In FIG. 5, processes 505, 506, and 512 may be considered to represent the filter coefficient generation 302 described in FIG. 3, as indicated with a dashed box labeled "302" around these processes in FIG. 5. On the other hand, processes 508 and 540 may be considered to represent, respectively, the signal conditioning 304 described in FIG. 3 (as indicated with a dashed box labeled "304" around the process 508 in FIG. 5) and the vital sign determination and tracking 306 described in FIG. 3 (as indicated with a dashed box labeled "306" around the process 514 in FIG. 5).

Subtracting the filtered second signal 422 from the first signal 410, e.g., using the subtractor 406, to generate the filtered first signal 412 in the process 508 is only one example of using the noise contribution derived from the reference sensor data to condition the PPG signal. More generally, the signal conditioning 304 (as, e.g., performed in the process 508) can include any method for performing signal conditioning of the data samples of the PPG signal to, e.g., filter, remove, or mask, portions of the data samples of the first signal which are likely associated with motion-related artifacts based on the filter 402 configured to generate filtered reference signal containing mostly, or only, the noise contribution. For example, in some embodiments, the process 508 may include applying filter coefficients generated for filtering the second signal to remove corresponding noise components from the first signal.

Although not specifically shown in FIG. 5, in some embodiments, the method 500 may further include some pre-processing filtering of one or both of the first signal 410 and the second signal 420. For example, in some embodiments where a heart rate is to be determined, a filter may be applied to one or both of these signals to filter out contributions in each of these signals that cannot be attributable to a heartbeat. Such a filter may, e.g., be a respective or a common band-pass filter, configured to filter out components outside of an expected range of frequencies representative of the heartbeat. Typically, a heart rate is between 0.5 Hertz to 3.5 Hertz (in some cases it can be as high as 4 or 5 Hertz). If the first and second signals have prominent components outside of the reasonable frequency band of interest, it is likely the data samples do not have a trackable heartbeat. Such components may be removed or attenuated using a band-pass filter. In another example, a filter may be applied to one or both of the first and second signals to remove or attenuate signal content indicative of a saturation condition of the respective sensor that generated the signal. In general, any of such pre-processing filtering may be performed any suitable point in time, but preferably before the process 514. In some embodiments, any of such pre-processing filtering can be incorporated with a signal conditioning process by processing the data samples with a filter to substantially attenuate signal content outside of a reasonable frequency band of interest corresponding to the heart rate (or apply a masking process to achieve a similar effect) before extracting the heart rate information of the first signal.

While some of the pre-processing filters are described above as band-pass filters (e.g., passing signals in the bandwidth from 0.5-3.5 Hertz, 0.5-4 Hertz, 0-4.5 Hertz, or similar variant thereof), in other embodiments, such filters can be implemented as a low-pass filter (e.g., passing signals in a bandwidth from 0-3.5 Hertz, 0-4 Hertz, 0-4.5 Hertz or similar variant thereof). The type of filter used to attenuate signals outside of the reasonable frequency band of interest can vary depending on the application. Furthermore, the reasonable frequency band of interest can vary depending on the application. In one example, the reasonable frequency band of interest includes a frequency band of 0.5 Hertz to 3.5 Hertz (or includes frequencies between 0.5 Hertz to 3.5 Hertz), which is suitable for keeping frequency content that is more likely to be associated with a heartbeat.

While some discussions are provided above with reference to FIR filters, embodiments of the present disclosure are applicable to other filter structures. Similarly, while some discussions are provided above with reference to LMS algorithm, LMS merely provides one example way of updating a filter and, in other embodiments, other adaptive algorithms with minor modifications that would be apparent to a skilled person based on the discussions provided herein may be used within the adaptive algorithm 404. In particular, adaptive algorithms that may be higher performing than LMS may be implemented as the adaptive algorithm 404, even though such algorithms may be more complex.

While some discussions are provided above with reference to a single type of reference sensor, in various other embodiments, measurements of two or more different types of reference sensors may be used, e.g., measurements of a biopotential sensor and measurements of a bioimpedance or a capacitive sensor. Furthermore, more than one optical sensor may be used and data obtained therefrom may be filtered according to the improved filtering method described above.

Select Examples

Example 1 provides an apparatus for determining a heart rate of a living being, the apparatus including a light source configured to generate light to illuminate a portion of a tissue of a living being, and an optical sensor configured to generate a first signal, the first signal including a tissue contribution indicative of at least a portion of the light generated by the light source that has interacted with the tissue (where the "tissue contribution" may also be referred to as a "heartbeat contribution" because it includes a contribution to the first signal that is due to the heartbeat activity of the living being and is, therefore, indicative of the heart rate of the living being). The apparatus further includes a reference sensor configured to generate a second signal, the second signal including a reference contribution and a noise contribution (where the noise contribution may include information related to the movement, or relative movement between the apparatus and the tissue). The apparatus also includes means for generating a filtered first signal based on the second signal, and means for determining the heart rate based on the filtered first signal.

Example 2 provides the apparatus according to example 1, where means for generating the filtered first signal includes means for attenuating (e.g., reducing or eliminating) the reference contribution in the second signal to generate a filtered second signal (thus, the filtered second signal is the second signal in which the reference contribution is attenuated, leaving substantially only the noise contribution of the second signal in the filtered second signal), and means for generating a filtered first signal based on the filtered second signal (e.g., by subtracting the filtered second signal from the first signal to generate the filtered first signal, or by using filter coefficients used to generate the filtered second signal to generate filter coefficients for filtering the first signal).

Example 3 provides the apparatus according to example 2, where the means for attenuating the reference contribution in the second signal includes a FIR filter.

Example 4 provides the apparatus according to examples 2 or 3, where the means for attenuating the reference contribution in the second signal is configured to apply adaptive linear prediction to the second signal to determine a set of filter coefficients configured to attenuate the reference contribution in the second signal.

Example 5 provides the apparatus according to example 4, where the adaptive linear prediction is based on a LMS update algorithm, e.g., a power-normalized LMS update algorithm.

Example 6 provides the apparatus according to example 5, where an update equation of the power-normalized LMS update algorithm includes a feedback coefficient.

Example 7 provides the apparatus according to examples 2 or 3, further including means for using the filtered first signal to adapt filter coefficients used for attenuating the reference contribution in the second signal.

Example 8 provides the apparatus according to example 7, further including, prior to determining the heart rate based on the filtered first signal, iterating a sequence of attenuating the reference contribution in the second signal to generate the filtered second signal, subtracting the filtered second signal from the first signal to generate the filtered first signal, and using the filtered first signal to adapt filter coefficients used for attenuating the reference contribution in the second signal.

Example 9 provides the apparatus according to examples 7 or 8, where using the filtered first signal to adapt filter coefficients used for attenuating the reference contribution in the second signal includes adapting the filter coefficients to minimize the filtered first signal.

Example 10 provides the apparatus according to any one of the preceding examples, further including a pre-processing filter configured to substantially attenuate, in the first signal, before generating the filtered first signal, signal content outside of a reasonable frequency band of interest corresponding to the heart rate.

Example 11 provides the apparatus according to any one of the preceding examples, further including a pre-processing filter configured to substantially attenuate, in the first signal, before generating the filtered first signal, signal content indicative of a saturation condition of the optical sensor.

Example 12 provides the apparatus according to any one of the preceding examples, further including a pre-processing filter configured to substantially attenuate, in the second signal, before generating the filtered second signal, signal content which is outside of an expected range for the filtered second signal.

Example 13 provides the apparatus according to any one of the preceding examples, where the apparatus is a wearable or a portable apparatus.

Example 14 provides the apparatus according to any one of the preceding examples, where the reference sensor is a biopotential sensor, and the reference contribution is a biopotential contribution indicative of a biopotential measured at a portion of the tissue of the living being (where, in various embodiments, portion of the tissue on which biopotential measurements are performed may be, but does not have to be substantially the same, or at least partially overlapping, with the portion of the tissue from which the light generated by the light source of said apparatus is reflected).

Example 15 provides the apparatus according to any one of the preceding examples, where the reference sensor is a bioimpedance sensor, and the reference contribution is a bioimpedance contribution indicative of a bioimpedance measured at a portion of the tissue of the living being (where, in various embodiments, portion of the tissue on which bioimpedance measurements are performed may be, but does not have to be substantially the same, or at least partially overlapping, with the portion of the tissue from which the light generated by the light source of said apparatus is reflected).

Example 16 provides the apparatus according to any one of the preceding examples, where the reference sensor is a capacitive sensor, and the reference contribution is a capacitive contribution indicative of a capacitance measured at a portion of the tissue of the living being (where, in various embodiments, portion of the tissue on which capacitance measurements are performed may be, but does not have to be substantially the same, or at least partially overlapping, with the portion of the tissue from which the light generated by the light source of said apparatus is reflected).

Example 17 provides a method for assisting determination of a vital sign (i.e., a physiological parameter) of a living being. The method includes using an optical sensor to generate a PPG signal for a first portion of a tissue of the living being, and using a reference sensor to generate a reference sensor signal for a second portion of the tissue of the living being (where, in various embodiments, the first and second portions may be completely different portions, may be the same portions, or may be portions which partially overlap), where the reference sensor is one of a biopotential sensor, a bioimpedance sensor, and a capacitive sensor. The method also includes using an adaptive filtering algorithm to generate a filtered second signal that includes the second signal in which one or more contributions indicative of a reference parameter that the reference sensor is designed to sense are attenuated, and generating a filtered first signal based on the filtered second signal and/or on one or more parameters of the adaptive filtering algorithm (e.g., based on the filter coefficients of the adaptive filtering algorithm).

Example 18 provides the method according to example 17, further including determining the vital sign of the living being based on the filtered first signal.

In various further examples, the method according to examples 17 or 18 may further include processes according to any of the preceding examples, e.g., of any of examples 1-16. In various further examples, the method according to examples 17 or 18 may be implemented using at least portions of the apparatus according to any of the preceding examples, e.g., of any of examples 1-16. In some further examples, any of such methods may further include outputting (e.g., displaying on a display or providing as an output of any other output device) the filtered first signal, or a representation thereof, and/or the determined vital sign, or a representation thereof. In still further examples, any of such methods may further include operating a hardware device, e.g. a medical device, based on the determined vital sign or a representation thereof. For example, such "operating" may include changing operating parameters of the hardware device, thereby changing how the device operates.

Example 19 provides a non-transitory computer readable storage medium storing software code portions configured for, when executed on a hardware processor, control operation of a heart rate monitoring apparatus by controlling an optical sensor to generate a PPG signal for a first portion of a tissue of the living being; controlling a reference sensor to generate a reference sensor signal for a second portion of the tissue of the living being (where, in various embodiments, the first and second portions may be completely different portions, may be the same portions, or may be portions which partially overlap), where the reference sensor is one of a biopotential sensor, a bioimpedance sensor, and a capacitive sensor; controlling an adaptive filtering algorithm to generate a filtered second signal that includes the second signal in which one or more contributions indicative of a reference parameter that the reference sensor is designed to sense are attenuated; and generating a filtered first signal based on the filtered second signal and/or on one or more parameters of the adaptive filtering algorithm (e.g., based on the filter coefficients of the adaptive filtering algorithm).

Example 20 provides the non-transitory computer readable storage medium according to example 19, where controlling operation of the heart rate monitoring apparatus further includes one or more processes for operating a heart rate monitoring apparatus according to the method of any one of the preceding examples.

Example 21 provides an apparatus for determining a heart rate of a living being, the apparatus including a first sensor configured to generate a first signal, the first signal including a contribution indicative of the heart rate of the living being, and a second sensor configured to generate a second signal, the second signal including a contribution indicative of a physiological parameter of the living being other than the heart rate. The apparatus further includes means for reducing noise in the first signal based on the second signal to generate a filtered first signal, and means for determining the heart rate based on the filtered first signal.

Example 22 provides the apparatus according to example 21, where the second signal does not include contributions indicative of the heart rate of the living being.

In various further examples, the first sensor of the apparatus according to examples 21 or 22 may be the optical sensor of the apparatus according to any one of examples 1-16, and/or the second sensor of the apparatus according to examples 21 or 22 may be the reference sensor of the apparatus according to any one of examples 1-16, and/or the means for reducing noise in the first signal of the apparatus according to examples 21 or 22 may be the means for generating the filtered first signal of the apparatus according to any one of examples 1-16. In some further examples, the apparatus according to examples 21 or 22 may further include a light source as the light source of the apparatus according to any one of examples 1-16. In still further examples, the apparatus according to examples 21 or 22 may further include other components and/or operate as the apparatus according to any one of examples 1-16. In some examples, the apparatus according to examples 21 or 22 may implement the method according to any one of the preceding examples, and/or include the non-transitory computer readable storage medium according to any of the preceding examples.

VARIATIONS AND IMPLEMENTATIONS

It is envisioned that a vital sign monitoring apparatus as described herein, configured to implement techniques for reducing motion-related artifacts in optical measurements using reference sensor measurements as described herein, can be provided in many areas including medical equipment, security monitoring, patient monitoring, healthcare equipment, medical equipment, automotive equipment, aerospace equipment, consumer electronics, and sports equipment, etc.

In some cases, the vital sign monitoring apparatus and techniques as described herein can be used in professional medical equipment in a healthcare setting such as doctor's offices, emergency rooms, hospitals, etc. In some cases, the vital sign monitoring apparatus and techniques as described herein can be used in less formal settings, such as schools, gyms, homes, offices, outdoors, under water, etc. In some cases, the vital sign monitoring apparatus and techniques as described herein can be provided in a consumer healthcare product.

The vital sign monitoring apparatus as described herein, or parts thereof, can take many different forms. Examples include watches, rings, wristbands, chest straps, headbands, headphones, ear buds, clamps, clips, clothing, bags, shoes, glasses, googles, hats, suits, necklace, attachments/patches/strips/pads which can adhere to a living being, accessories, portable devices, and so on. In particular, wearables technology (or referred often as "wearables", i.e., electronics which are intended to be worn by humans or other living beings) can greatly leverage the benefits of the vital sign monitoring apparatus disclosed herein due to the wearables' portability and the robustness of the disclosed techniques against motion artifacts. Even in the presence of noise, the wearable can effectively determine or track a heart rate, or other suitable vital sign of interest. Besides wearables, portable or mobile devices such as mobile phones and tablets can also include a processor having the functions related to reducing motion-related artifacts in optical measurements using reference sensor measurements as described herein, an analog front end, a light source, a light sensor, and a reference sensor as described herein (or an extension, either wired or wireless, having any one or more of the light source, the light sensor, and the reference sensor) to provide a vital sign monitoring apparatus as described herein. In this manner, users can advantageously use ubiquitous mobile phones to make measurement of various vital signs. Furthermore, it is envisioned that the vital sign monitoring apparatus as described herein can be used in wired or wireless accessories such as cuffs, clips, straps, bands, probes, etc., to sense various physiological parameters of a living being. These accessories can be connected to a machine configured to provide the processor and the analog front end. In various embodiments, the analog front end could be provided in the accessory or in the machine.

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure. For instance, instead of processing the signals in the digital domain, it is possible to provide equivalent electronics that can process the signals in the analog domain.

In one example embodiment, any number of electrical circuits of the FIGS. may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer readable storage medium comprising instructions to allow a processor to carry out those functionalities. In some cases, application-specific hardware can be provided with or in the processor to carry out those functionalities.

In another example embodiment, the electrical circuits of the FIGS. may be implemented as stand-alone modules (e.g., a device with associated components and circuitry configured to perform a specific application or function) or implemented as plug-in modules into application-specific hardware of electronic devices. Note that particular embodiments of the present disclosure may be readily included in a system on chip (SOC) package, either in part, or in whole. An SOC represents an integrated circuit (IC) that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the functionalities described herein, in particular, the functionalities related to reducing motion-related artifacts in optical measurements using reference sensor measurements, may be implemented in one or more silicon cores in Application-Specific Integrated Circuits (ASICs), Field Programmable Gate Arrays (FPGAs), and other semiconductor chips.

Note that the activities discussed above with reference to the FIGS. are applicable to any integrated circuits that involve signal processing, particularly those that can execute specialized software programs, or algorithms, some of which may be associated with processing digitized real-time data to track a heart rate. Certain embodiments can relate to multi-DSP signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems. Moreover, certain embodiments discussed above can be provisioned in digital signal processing technologies for medical imaging, patient monitoring, medical instrumentation, and home healthcare. This could include pulmonary monitors, heart rate monitors, pacemakers, etc.

Note that with the numerous examples provided herein, interaction may be described in terms of two, three, four, or more parts. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of the present disclosure. In certain cases, it may be easier to describe one or more of the functionalities of a given set of flows by only referencing a limited number of electrical elements. It should be appreciated that the features of the FIGS. and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in the present disclosure, references to various features (e.g., elements, structures, modules, components, steps, operations, parts, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to reducing motion-related artifacts in optical measurements using reference sensor measurements, illustrate only some of the possible functions that may be executed by, or within, systems illustrated in the FIGS. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure. Note that all optional features of the apparatus described above may also be implemented with respect to the method or process described herein and specifics in the examples may be used anywhere in one or more embodiments.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the present disclosure, to limit this disclosure in any way that is not otherwise reflected in the appended claims.

Note that all optional features of the apparatus described above may also be implemented with respect to the method or process described herein and specifics in the examples may be used anywhere in one or more embodiments.

The invention claimed is:

1. An apparatus for determining a heart rate of a living being, the apparatus comprising:
    an optical sensor configured to generate a first signal, the first signal comprising a tissue contribution indicative of at least a portion of light generated by a light source configured to generate a light to illuminate a portion of a tissue of the living being, the portion of light being the light that has interacted with the tissue;
    a reference sensor configured to generate a second signal, the second signal comprising a reference contribution and a noise contribution, where the reference contribution is indicative of a further physiological parameter of the living being, the further physiological parameter is measured by the reference sensor, the physiological parameter and the further physiological parameter being different types of physiological parameters, and where the noise contribution is indicative of noise in the second signal; and
    one or more circuits configured to:
        attenuate the reference contribution in the second signal to generate a filtered second signal,
        generate a filtered first signal based on the filtered second signal, and
        determine the heart rate based on the filtered first signal.

2. The apparatus according to claim 1, wherein the one or more circuits configured to attenuate the reference contribution in the second signal include a finite impulse response (FIR) filter.

3. The apparatus according to claim 1, wherein the one or more circuits configured to attenuate the reference contribution in the second signal are configured to apply adaptive linear prediction to the second signal to determine a set of filter coefficients configured to attenuate the reference contribution in the second signal.

4. The apparatus according to claim 3, wherein the adaptive linear prediction is based on a least mean square (LMS) update algorithm.

5. The apparatus according to claim 4, wherein an update equation of the power-normalized LMS update algorithm includes a feedback coefficient.

6. The apparatus according to claim 1, wherein the one or more circuits are further configured to use the filtered first signal to adapt filter coefficients used for attenuating the reference contribution in the second signal.

7. The apparatus according to claim 6, wherein the one or more circuits are further configured to, prior to determining the heart rate based on the filtered first signal, iterate a sequence of:
    attenuating the reference contribution in the second signal to generate the filtered second signal,
    subtracting the filtered second signal from the first signal to generate the filtered first signal, and
    using the filtered first signal to adapt filter coefficients used for attenuating the reference contribution in the second signal.

8. The apparatus according to claim 6, wherein using the filtered first signal to adapt filter coefficients used for attenuating the reference contribution in the second signal includes adapting the filter coefficients to minimize the filtered first signal.

9. The apparatus according to claim 1, further comprising:
    a pre-processing filter configured to attenuate, in the second signal, before generating the filtered second signal, signal content which is outside of an expected range for the filtered second signal.

10. The apparatus according to claim 1, wherein the apparatus is a wearable or a portable apparatus.

11. The apparatus according to claim 1, wherein the reference sensor is a biopotential sensor, and the reference contribution is a biopotential contribution indicative of a biopotential at a portion of the tissue of the living being.

12. The apparatus according to claim 1, wherein the reference sensor is a bioimpedance sensor, and the reference contribution is a bioimpedance contribution indicative of a bioimpedance measured at a portion of the tissue of the living being.

13. The apparatus according to claim 1, wherein the reference sensor is a capacitive sensor, and the reference contribution is a capacitive contribution indicative of a capacitance measured of a portion of the tissue of the living being.

14. The apparatus according to claim 1, wherein attenuating the reference contribution in the second signal includes attenuating the reference contribution in the second signal to substantially eliminate the reference contribution in the second signal.

15. The apparatus according to claim 1, further comprising the light source.

16. The apparatus according to claim 1, wherein the physiological parameter is one of a heart rate, an oxygen saturation, a blood pressure, a respiratory rate, or a physiological parameter indicative of a movement of the living being.

17. A method for assisting determination of a vital sign of a living being, the method comprising:
   controlling an optical sensor to generate a photoplethysmography (PPG) signal for a first portion of a tissue of the living being;
   controlling a reference sensor to generate a reference sensor signal for a second portion of the tissue of the living being, where the reference sensor signal includes a reference contribution indicative of at least one of a biopotential, a bioimpedance, and a capacitance of the second portion of the tissue;
   controlling a filtering algorithm to generate a filtered reference sensor signal that includes the reference sensor signal in which the reference contribution has been attenuated; and
   generating a filtered PPG signal that includes the PPG signal filtered based on the filtered reference sensor signal.

18. The method according to claim 17, further comprising:
   determining the vital sign of the living being based on the filtered PPG signal.

19. The method according to claim 17, wherein the vital sign is one of a heart rate, an oxygen saturation, a blood pressure, a respiratory rate, or a physiological parameter indicative of a movement of the living being. signal.

20. An apparatus for determining a first physiological parameter of a living being, the apparatus comprising:
   a first sensor configured to generate a first signal, the first signal comprising a contribution indicative of the first physiological parameter of the living being;
   a second sensor configured to generate a second signal, the second signal comprising a contribution indicative of a second physiological parameter of the living being, the second physiological parameter and the first physiological parameter being physiological parameters of different types; and
   one or more circuits configured to:
      attenuate the contribution indicative of the second physiological parameter in the second signal to generate a filtered second signal,
      generate a filtered first signal by reducing noise in the first signal based on the filtered second signal, and
      determine the first physiological parameter based on the filtered first signal.

21. The apparatus according to claim 19, wherein the first sensor is an optical sensor configured to generate the first signal based on illumination of a portion of a tissue of the living being.

22. The apparatus according to claim 20, wherein the first physiological parameter is one of a heart rate, an oxygen saturation, a blood pressure, a respiratory rate, or a physiological parameter indicative of a movement of the living being.

23. The apparatus according to claim 20, wherein the second physiological parameter is at least one of a biopotential, a bioimpedance, and a capacitance of the living being.

* * * * *